United States Patent [19]

Cooley et al.

[11] 4,032,458

[45] June 28, 1977

[54] PRODUCTION OF 1,4-BUTANEDIOL

[75] Inventors: Stone D. Cooley, Houston; Robert P. Arganbright, Seabrook; William G. Bowman, Pasadena; James D. Henery, Houston, all of Tex.

[73] Assignee: Petro-Tex Chemical Corporation, Houston, Tex.

[22] Filed: Aug. 8, 1975

[21] Appl. No.: 602,993

[52] U.S. Cl. .................... 260/635 D; 260/485 R; 260/637 R; 260/643 D
[51] Int. Cl.² ......................................... C07C 29/00
[58] Field of Search ....... 260/635 D, 485 R, 637 R, 260/643 D

[56] References Cited

UNITED STATES PATENTS

| | | | |
|---|---|---|---|
| 2,091,800 | 8/1937 | Adkins et al. | 260/635 D |
| 2,322,099 | 6/1943 | Schmidt | 260/635 D |
| 3,088,982 | 5/1963 | Feldman et al. | 260/643 D |
| 3,268,588 | 8/1966 | Horlenko et al. | 260/635 D |
| 3,478,103 | 11/1969 | Hann | 260/635 D |
| 3,830,830 | 8/1974 | Cleveland et al. | 260/485 R |
| 3,852,164 | 12/1974 | Chow et al. | 260/637 R |
| 3,862,147 | 1/1975 | Cooley et al. | 260/485 R |
| 3,917,720 | 11/1975 | Webb et al. | 260/637 R |

OTHER PUBLICATIONS

Adkins et al. "J. Am. Chem. Soc.," vol. 70 (1948), pp. 3121–3125.

Primary Examiner—Joseph E. Evans
Attorney, Agent, or Firm—Kenneth H. Johnson; N. Elton Dry

[57] ABSTRACT

An improved process is disclosed wherein 1,4-butanediol is produced from a maleic acid-containing solution in a multistep process comprising esterification of maleic acid at elevated temperature and pressure in the presence of a monohydric alcohol to form dialkyl esters of maleic acid, hydrogenation of the dialkyl esters to 1,4-butanediol in a two-step hydrogenation process, recovery of the 1,4-butanediol substantially free from other close boiling contaminants in an extraction zone and recovering 1,4-butanediol in high purity from a distillation zone operated at reduced pressure.

5 Claims, 1 Drawing Figure

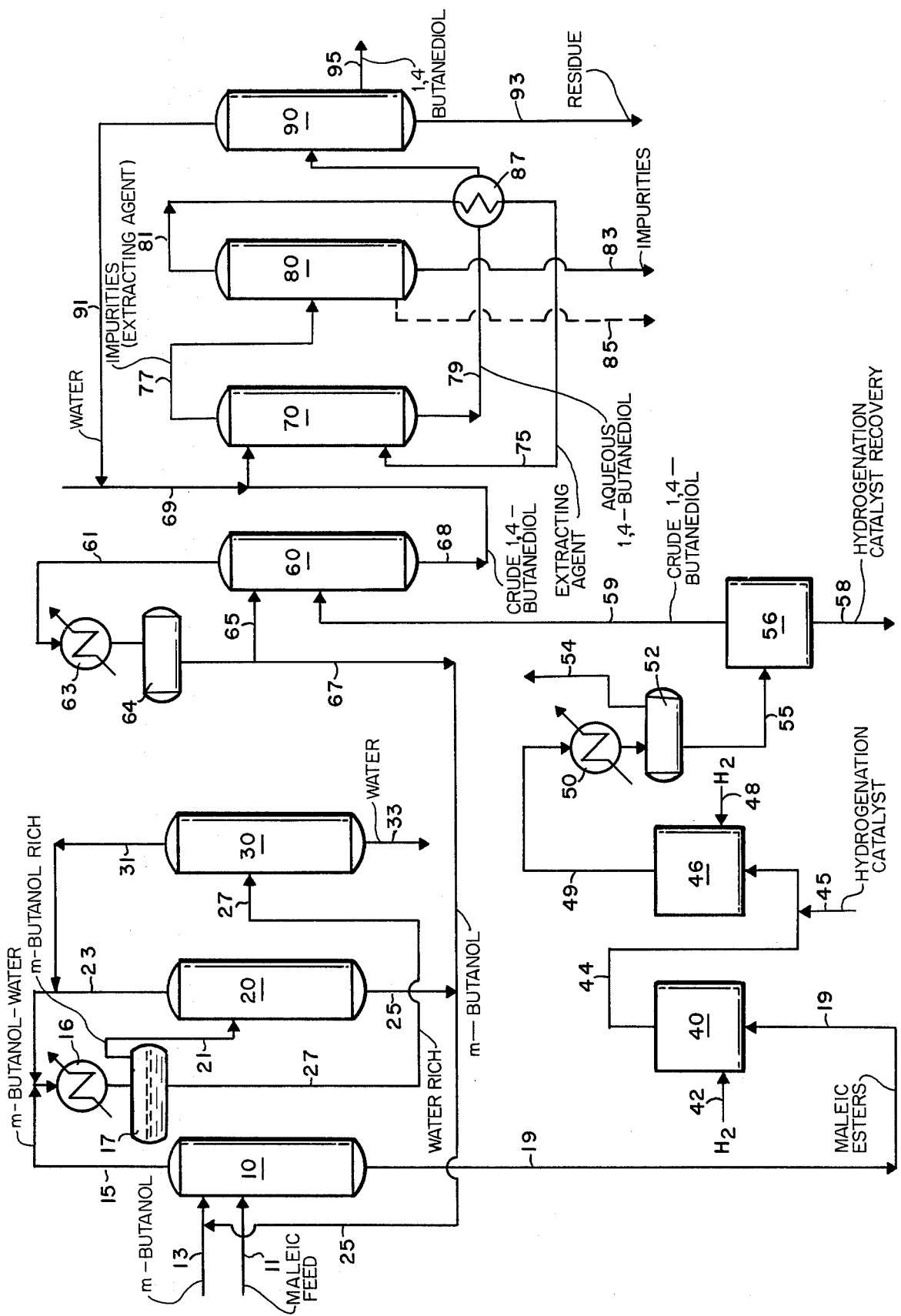

PRODUCTION OF 1,4-BUTANEDIOL

BACKGROUND OF THE INVENTION

1. Field Of The Invention

This invention relates to an improved method for the production of 1,4-butanediol. More particularly, this invention relates to a method for converting a maleic acid-containing mixture to a substantially anhydrous mixture comprising 1,4-butanediol which is thereafter recovered from the mixture in high purity.

2. Description Of The Prior Art 1,4-Butanediol is a monomer used in the production of polybutylene terephthalate, a unique engineering plastic. Butanediol has been manufactured commercially by processes involving the Reppe reaction of acetylene and formaldehyde followed by hydrogenation of the reaction mixture. Other processes for the production of 1,4-butanediol involve the hydrolysis of dichlorobutanes or the hydrogenation of maleic anhydride.

Processes for the production of esters from maleic acid or maleic anhydride generally involve the acid catalyzed esterification of the maleic precursor to a dialkyl ester. Such processes suffer from the disadvantage that the acidic catalysts are difficult to remove from the product and even small amounts of acid in the ester product make it unsuitable for use in catalytic processes for hydrogenating the ester to 1,4-butanediol.

Processes for the production of maleic acid or maleic anhydride generally involve the high temperature, catalytic oxidation of hydrocarbons, e.g., benzene, to form an effluent gas comprising maleic acid and maleic anhydride. Such effluent gases from the reaction zone are generally quenched or scrubbed with water thereby forming an aqueous solution comprising maleic acid. Maleic acid or maleic anhydride is thereafter recovered from this aqueous maleic acid solution by a number of processing steps involving distillation, crystallization, and the like.

It is an object of the instant invention to provide a process for the conversion of maleic acid into its dialkyl esters without requiring the use of an esterification catalyst. It is also an object of this invention to provide a process for the production of dialkyl esters of maleic and fumaric acid which process does not require the use of high purity maleic acid or maleic anhydride. Finally, it is an object of this invention to provide a process for the production of dialkyl esters of maleic acid which employs crude aqueous maleic acid-containing mixtures such as those obtained in commercial processes for the production of maleic acid or maleic anhydride without the prior recovery and purification of the maleic acid or maleic anhydride.

SUMMARY OF THE INVENTION

In accordance with the instant invention, a maleic acid-containing mixture is converted into high purity 1,4-butanediol in a multistep process comprising a. contacting said maleic acid-containing mixture with a monohydric alcohol having from 2 to about 10 carbon atoms in an esterification-dehydration zone comprising a distillation column wherein the maleic acid is distilled in the presence of said monohydric alcohol thereby forming an overhead vapor product comprising an azeotrope of water and said monohydric alcohol and a bottoms product having an acid number of 1.0 mg KOH/g. or less and comprising said monohydric alcohol and dialkyl esters of maleic acid, b. contacting said bottoms product from the esterification-dehydration zone with hydrogen at elevated temperature and pressure in the presence of a copper chromite hydrogenation catalyst in a first hydrogenation zone thereby to hydrogenate the ethylenic unsaturation present in the aforesaid bottoms product from the esterification-dehydration zone, c. contacting the product from the first hydrogenation zone in a second hydrogenation zone with hydrogen in the presence of a copper chromite hydrogenation catalyst thereby effecting a reduction of the dialkyl esters to a product comprising 1,4-butanediol and the corresponding monohydric alcohol, d. introducing the reaction product from the second hydrogenation zone to a catalyst recovery zone wherein the copper chromite hydrogenation catalyst is recovered, e. introducing the product obtained from the catalyst recovery zone to a light ends recovery zone wherein there is recovered an overhead product comprising the monohydric alcohol and the more volatile impurities and a bottoms product comprising crude 1,4-butanediol and the less volatile impurities, and recovering 1,4-butanediol from said bottoms product of the light ends recovery zone.

BRIEF DESCRIPTION OF THE DRAWING

The invention will be illustrated by reference to the attached drawing which represents a schematic flow diagram of a preferred embodiment of the invention.

DESCRIPTION OF THE PREFERRED EMBODIMENTS

In accordance with the present invention, a maleic acid-containing liquid feedstock is introduced into a distillation zone wherein it is distilled in the additional presence of a monohydric alcohol. The monohydric alcohol is an esterification agent, reacting with the maleic acid to produce a mixture of dialkyl maleate and dialkyl fumarate. Additionally, the monohydric alcohol is a dehydrating agent and is selected for its ability to form an azeotrope with water thereby to facilitate the removal of water from the distillation zone.

The monohydric alcohols which are suitable in the practice of the process of this invention include monohydric alcohols having from 2 to about 10 carbon atoms. Preferred monohydric alcohols are those which form a heterogeneous azeotrope with water. Such heterogeneous azeotropic compositions upon condensing form two immiscible phases, an alcohol-rich phase and a water-rich phase. Monohydric alcohols which form heterogeneous azeotropes with water include n-butanol, primary isoamyl alcohol, and n-amyl alcohol. Especially preferred in the practice of this invention is n-butanol.

The maleic acid-containing feedstocks, which are the subject of this invention, include maleic acid, maleic anhydride and fumaric acid. Also suitable are aqueous maleic acid solutions having from about 10 to about 60 wt. % maleic acid, and preferably from about 30 to about 50 wt. % maleic acid, which solutions can contain other impurities commonly associated with the production of maleic acid. For example, a typical feedstock is the maleic acid scrubber water solution obtained as an intermediate in a commercial process for the production of maleic acid by the air oxidation of a hydrocarbon, e.g. benzene. Such maleic acid scrubber solutions generally contain a small proportion of fumaric acid, an isomer of maleic acid, formaldehyde and a small proportion of other water soluble by-products from the oxidation reaction in which the maleic acid was produced. Examples of such impurities include aliphatic monocarboxylic acids having from about 2 to about 6 carbon atoms and aliphatic aldehydes having from about 2 to about 6 carbon atoms.

In the process of this invention, the maleic acid contained in the feedstock is converted to dialkyl esters of maleic acid, including both dialkyl maleate and dialkyl fumarate. Both the maleate and fumarate esters are hydrogenated to the same product, namely 1,4-butanediol. Therefore, the maleic acid-containing feedstock can include fumaric acid from sources other than that contained in the maleic acid-containing feedstock. For example, in the commercial production of maleic anhydride a substantial quantity of maleic acid or anhydride is lost by isomerization to fumaric acid which accumulates as a solid phase in storage tanks. This solid fumaric acid may be recovered from the storage tanks, and employed in the process of this invention. Still another source of feedstock for the process of this invention is the distillation column bottoms from the final distillation of maleic anhydride, which bottom stream consists essentially of fumaric acid and maleic anhydride. This bottoms stream can likewise be employed as the maleic acid feedstock in the practice of this invention.

The maleic acid-containing mixture is introduced into an intermediate portion of the esterification-dehydration zone comprising a distillation column wherein it is distilled in the presence of the monohydric alcohol hereinbefore described. The alcohol serves both as a dehydrating agent and an esterification agent in forming the dialkyl esters. The alcohol is generally introduced into the distillation column at a point near the top of the column and the dialkyl ester-containing product is recovered from the distillation column as a bottoms product. The water formed as a result of the esterification reaction and any water contained in the maleic acid-containing feedstock are removed in an overhead vapor product from the distillation column. The composition of the overhead vapor product will depend upon the choice of monohydric alcohol selected, but in any case the water is distilled from the distillation column as an azeotrope in combination with the monohydric alcohol. The monohydric alcohol is generally recovered from this azeotropic composition, as will be hereinafter explained, and is returned to the distillation column for reuse.

The overhead pressure of the distillation column is selected such that the temperature in the lower portion of the distillation column is high enough to enable completion of the esterification reaction at a rate suitable for a commercial process. Additionally, the distillation column must be efficient such that the lower portion of the distillation column is substantially free of water. By substantially free of water is meant that the free water contained in the aqeous maleic acid-containing feedstock has been distilled out of the mixture at a point in the distillation column above this lower portion of the column and that the small amounts of water which are formed as the esterification reaction occurs in this lower portion of the distillation column are quickly distilled upwards from that portion of the column. Thus, the concentration of water present in the lower portion of the distillation column where the bulk of the esterification reaction occurs, is extremely low and gets progressively lower towards the bottom of the distillation column at which point the esterification of the maleic acid and fumaric acid has been substantially completed.

The pressure which must be established in the distillation column in order to produce the temperature necessary to complete esterification, will depend of course upon the choice of dehydrating agent. The necessary operating pressure will be highest whenever the dehydrating agent is ethanol and will decrease as the molecular weight of the monohydric alcohol increases. In a preferred embodiment of the process of this invention, employing n-butanol as the dehydrating agent, a pressure of from about 55 to about 80 psig is employed in order to maintain the temperature in the lower portion of the distillation column at a temperature of from about 175° C. to about 235° C., and preferably from about 190° C. to about 220° C. By lower portion of the distillation column is meant that portion which provides sufficient residence time in the column at the aforementioned desired conditions to ensure substantially complete conversion of the maleic acid and fumaric acid to the corresponding dialkyl esters. Generally, this represents approximately the lower one-third of the distillation column although a greater proportion of the column may be required for some embodiments of this invention. At any rate, that portion of the column in which the maleic acid and fumaric acid need to be in contact with the monohydric alcohol in the substantial absence of free water to effect the esterification, can be readily determined empirically without undue experimentation as will be apparent to one skilled in the art.

As previously mentioned, the overhead vapor product from the distillation column comprises water and the monohydric alcohol in an azeotropic composition. It is desirable to recover the monohydric alcohol from the azeotropic mixture and return it to the distillation column as a reflux. However, the manner in which the monohydric alcohol is recovered from the azeotropic composition will depend upon whether the azeotrope recovered from the distillation column is a heterogeneous azeotrope or a homogeneous azeotrope. Some monohydric alcohols, such as ethanol and n-propanol, for example, form a minimum boiling azeotropic mixture with water, which upon condensation exist as a single homogeneous liquid phase. By contrast, monohydric alcohols such as n-butanol and isoamyl alcohol, for example, form an azeotropic composition with water, which upon condensation separates into two immiscible liquid phases: an alcohol-rich phase and a water-rich phase. The relative proportions of alcohol and water in each of the two immiscible phases will depend upon the temperature at which the azeotropic mixture is condensed.

The process of this invention wherein a monohydric alcohol is employed that forms a heterogeneous azeotrope with water is preferred. In such a process the alcohol-rich phase which is obtained upon condensation of the overhead product from the esterification zone has an alcohol concentration greater than the alcohol concentration in the azeotropic overhead product. Distillation of this alcohol-rich phase in an alcohol recovery zone produces an overhead vapor product in which the alcohol and water are present in the azeotropic proportions and a bottoms product which is substantially anhydrous monohydric alcohol. This bottoms product is recycled to the esterification-dehydration zone for reuse in the esterification-dehydration process.

The water-rich phase which is obtained upon condensation of the overhead product from the esterification-dehydration zone has a water concentration which is greater than the water concentration in the azeotropic overhead product. Distillation of the water-rich phase in a dehydration zone produces an overhead vapor product in which the alcohol and water are present in azeotropic proportions and a bottoms product which is substantially water. The overhead vapor azeotropic products obtained from each of the aforementioned distillations are combined with the overhead vapor product from the esterification-dehydration zone. In this manner, substantially all of the contained monohydric alcohol is recovered in the process.

Whenever the monohydric alcohol employed in practicing the process of this invention results in the formation of a homogeneous azeotropic composition being recovered from the distillation column, it is necessary to add a third component to the condensed overhead in order to recover the monohydric alcohol. This third component is selected for its ability to form a heterogeneous ternary azeotrope with the alcohol-water mixture. Examples of suitable third components include benzene and toluene.

In such a ternary system, the overhead product from the esterification-dehydration zone is combined with the third component and is subjected to distillation in the alcohol recovery zone. The bottoms product from this distillation comprises substantially monohydric alcohol and is recycled to the esterification-dehydration zone. A side draw obtained from a lower portion of the alcohol recovery zone comprising the third component as a major constituent and a minor amount of the monohydric alcohol is recycled for combination with the feed to the alcohol recovery zone.

The overhead product from the alcohol recovery zone is a ternary azeotrope, which upon condensation separates into two immiscible layers. The lower layer is a water-rich layer additionally containing minor proportions of monohydric alcohol and the third component. The upper layer is rich in the third component with minor proportions of the monohydric alcohol and water.

This upper layer is recycled and combined with the overhead product from the esterification-dehydration zone. The lower water-rich layer is subjected to a distillation in a dehydration zone in which water is recovered as a bottoms product and a ternary azeotrope is recovered as the overhead product. This overhead product is combined with the ternary azeotrope recovered as the overhead product from the alcohol recovery zone. In this manner, substantially all of the monohydric alcohol and third component are recovered.

The crude dialkyl ester product obtained as the bottoms product from the esterification-dehydration zone comprises dialkyl maleate, dialkyl fumerate and monohydric alcohol. In the process of this invention, the esterification of the maleic acid and fumaric acid employed as the feedstock is essentially complete. Generally, the acid number of the bottoms product from this esterification-dehydration zone is 1.0 mg KOH/g or less, with an acid number of approximately 0.2 mg KOH/g or less being preferred.

In a first hydrogenation zone, the dialkyl ester-containing product from the esterification-dehydration zone is contacted at elevated temperature and pressure with hydrogen in the presence of a copper chromite hydrogenation catalyst. The maleic and fumaric unsaturation is hydrogenated thereby forming the corresponding dialkyl succinate esters. This hydrogenation reaction is an exothermic reaction and the reaction conditions must be carefully controlled. Although only one mole of hydrogen is required for each mole of olefinic unsaturation present in the dialkyl esters, generally the hydrogenation reaction is carried out in the presence of excess hydrogen.

The hydrogenation catalyst employed in the process of this invention is generally referred to as a copper chromite hydrogenation catalyst. However, as will be apparent to one skilled in the art, the term copper chromite is commonly used to refer to mixtures of oxides of copper and chromium, for example, a mixture of cupric oxide and chromic oxide. It is also well-known in the art that such copper chromite hydrogenation catalyst can additionally include other metals or metal oxides as promoters. For example, barium promoted copper chromite catalysts are commonly available.

The form in which the copper chromite catalyst is employed is not critical to the process of this invention. The catalyst is generally employed in a finely subdivided form but may also be employed as particles or chunks of larger size. The amount of catalyst and the operating conditions employed in the first hydrogenation zone must be carefully selected in order to control the exotherm resulting from the reaction. Generally, the copper chromite catalyst is employed in an amount of from about 0.5 to about 5.0 wt.%, based upon the amount of unsaturated dialkyl ester to be hydrogenated, with an amount of from about 1.0 to about 2.0 wt.% on the same basis being preferred. The temperature at which the hydrogenation reaction is carried out is generally in the range of from about 100° C. to about 200° C., with a temperature of from about 140° C. to about 160° C. being preferred. The reaction is carried out under a hydrogen pressure of from about 2,000 psig to about 3,500 psig. Higher pressures can be employed if desired although there is generally no incentive to employ such higher pressures.

In an embodiment of this invention wherein the copper chromite hydrogenation catalyst is employed in the form of a finely divided powder, it is desirable that the reaction mixture be subjected to vigorous agitation in order to ensure efficiency of the hydrogenation reaction and maintain a high selectivity for the formation of the desired products.

The residence time of the unsaturated dialkyl ester-containing feedstock in the hydrogenation zone will depend of course upon the catalyst concentration and the particular reaction conditions employed. Generally, in batch processes wheren the copper chromite hydrogenation catalyst is employed as a slurry in an amount hereinbefore described, residence times of from about 10 minutes to about 1 hour in the hydrogenation zone are satisfactory, with a residence time of from about 20 minutes to about 30 minutes being preferred.

Although not required in the hydrogenation process herein described, a solvent can be employed to facilitate control of the exothermic heat of reaction resulting from the hydrogenation process. A suitable solvent is the monohydric alcohol employed in preparing the dialkyl esters in the esterification-dehydration zone. For this reason, the crude dialkyl ester-containing product from that zone is employed in the first hydrogenation zone without removal of the monohydric alcohol contained in that crude product. Other suitable solvents include p-dioxane, tetrahydrofuran, and the like.

Although a small proportion of the dialkyl esters present in the first hydrogenation zone will undergo cleavage of the ester group with the resulting formation of a hydroxyl group, the major proportion of the conversion of the dialkyl esters to 1,4-butanediol occurs in the second hydrogenation zone. In this hydrogenation zone, the reaction conditions are more severe resulting in the conversion of a substantial proportion of the dialkyl succinate ester to a mixture of 1,4-butanediol and the corresponding monohydric alcohol. In this second hydrogenation zone, the reaction product from the first hydrogenation zone is again contacted with excess hydrogen at elevated temperature and pressure in the presence of a copper chromite hydrogenation catalyst in order to effect the conversion of dialkyl ester to 1,4-butanediol.

The catalyst employed in this second hydrogenation zone is generally the same copper chromite hydrogenation catalyst employed in the first hydrogenation zone. However, in the second hydrogenation zone, the catalyst is generally employed in an amount of from about 1.0 to about 10.0 wt.%, based upon the dialkyl succinate charged to the hydrogenation zone, with an amount of from about 3 to about 7 wt.% on the same basis being preferred.

In order to provide the severity of operating conditions required in order to convert substantially all of the dialkyl esters to 1,4-butanediol, an operating temperature in the range of from about 225° C. to about 300° C. is employed, with a temperature in the range of from about 250° C. to about 275° C. being preferred. The reaction is carried out in the presence of excess hydrogen at a pressure of from about 3,000 psig to about 4,000 psig. The residence time required in order to effect desired conversion is in the range of from about 0.5 to about 5.0 hours for batch processes, with a residence time of from about 1.0 to about 2.0 hours being preferred.

The crude 1,4-butanediol-containing product obtained from the second hydrogenation zone comprises, in addition to 1,4-butanediol and the monohydric alcohol obtained from the hydrogenation reaction, other impurities formed as by-products in the hydrogenation reaction. Illustrative of these impurities, when n-butanol is used as the monohydric alcohol in the process of this invention, are dibutyl succinate, dibutyl butoxy succinate, γ-butyrolactone, γ-hydroxybutyraldehyde, butoxy-1,4-butanediol and other higher molecular weight high boiling residues. In addition, the crude 1,4-butanediol-containing product will contain excess hydrogen, the copper chromite hydrogenation catalyst and a small proportion of light ends, including the γ-butyrolactone and the formal of the monohydric alcohol employed in the esterification-dehydration reaction.

The excess hydrogen is recovered from the crude 1,4-butanediol-containing mixture and is recycled for use in either of the hydrogenation zones. In batch processes wherein the crude 1,4-butanediol-containing mixture additionally contains the copper chromite hydrogenation catalyst in a finely divided form, the catalyst is recovered from the reaction mixture by conventional means, e.g. filtration, centrifugation and the like. The recovered copper chromite hydrogenation catalyst can be recycled to either of the hydrogenation zones in an amount sufficient to supply the catalyst necessary for that zone. It may be necessary to take a portion of the recovered catalyst and subject it to a regeneration process in order to maintain the catalyst system at the desired level of activity.

In a preferred embodiment of the process of this invention, the crude 1,4-butanediol-containing mixture now free of hydrogen and hydrogenation catalyst is subjected to a light ends distillation zone wherein the monohydric alcohol and other light ends materials are recovered as an overhead vapor product. This overhead product may be recycled to the esterification-dehydration zone for reuse according to the process of this invention.

The bottoms product from the light ends recovery zone comprises the 1,4-butanediol in admixture with a number of other reaction products from the hydrogenation of the dialkyl esters from which it was derived. For example, whenever n-butanol is employed in practicing the process of this invention and the dialkyl esters are the dibutyl esters, the following compounds are generally found in such crude butanediol mixtures in the following approximate concentrations:

| dibutyl succinate | 2.0–5.0 | mole % |
|---|---|---|
| dibutyl butoxysuccinate | 1.0–3.0 | mole % |
| γ-butyrolactone | 1.0–3.0 | mole % |
| γ-hydroxybutyraldehyde | 1.0 | mole % |
| Butoxy-1,4-butanediol | 2.0–4.0 | mole % |
| High boiling residues | 4.0–8.0 | wt. % |

In addition to the above impurities, there may be considerable quantities of butanol present if the light ends distillation as hereinbefore described is not efficient. It will be apparent to one skilled in the art, that although the foregoing description of the impurities present in a crude butanediol-containing mixture relate to butyl derivatives of maleic acid, this reflects merely the choice of alcohol used in the initial esterification reaction. Other suitable monohydric alcohols useful in the process of this invention include ethanol, propanol, butanol, amylalcohol, and the like. Butanol is a preferred monohydric alcohol employed in preparing the dialkyl esters from which the crude butanediol-containing mixture, which is the subject of this invention, is prepared.

According to the process of this invention, 1,4-butanediol is recovered from the crude 1,4-butanediol-containing mixture by extracting the major proportions of the aforementioned impurities from an aqueous mixture of the crude 1,4-butanediol and thereafter recovering the 1,4-butanediol in high purity in a distillation carried out at reduced temperature and pressure. Initially, the crude 1,4-butanediol-containing mixture is diluted with water to form an aqueous mixture having a water content of from about 5 to about 75 wt.% water, and preferably from about 20 to about 50 wt.%. It has been found that by adding water to the crude 1,4-butanediol-containing mixture improves the phase separation obtained between the aqueous phase and the hydrocarbon extract phase in the extraction zone. Moreover, maintaining a water concentration within the aforementioned range results in an improved extraction of impurities into the hydrocarbon extract phase.

In the extraction zone, the aqueous 1,4-butanediol-containing mixture is contacted with a hydrocarbon extracting agent which is immiscible with the aqueous 1,4-butanediol-containing mixture. Suitable hydrocarbon extracting agents which may be employed in practicing the process of this invention include alkanes having from about 6 to about 10 carbon atoms and aromatic hydrocarbons having from about 6 to about 8 carbon atoms. Examples of suitable hydrocarbon extracting agents include hexane, heptane, octane, benzene, toluene, and the like. It is preferable to select a hydrocarbon extracting agent with a relatively low boiling point, in that the hydrocarbon extract phase recovered from the extraction zone is subjected to a distillation to recover the hydrocarbon extracting agent. In this manner, it is possible to minimize the energy requirements necessary for the practice of this invention. For this reason, hexane and benzene are particularly preferred extracting agents.

In the extracting zone, the aqueous 1,4-butanediol-containing mixture is contacted with the extracting agent to effect the extraction of the impurities into the hydrocarbon extract phase. Thereafter, the two phases are separated. This extraction step can be effected by a variety of known methods. For example, a rotating disc contactor may be employed to effect the extraction, alternately, the aqueous 1,4-butanediol-containing mixture and the extracting agent may be intimately mixed by suitable mixing device and thereafter separated, as for example, by centrifugation or in a suitable settling zone which may include packing material in order to facilitate separation of the phases. A preferred embodiment of this invention which is illustrated in the attached figure, illustrates a continuous process, wherein the aqueous 1,4-butanediol-containing mixture is introduced at the top of the extraction zone and the extracting agent is introduced at the bottom of the extraction zone. The flow of the two streams is countercurrent through the extraction zone wherein they are brought into intimate contact to effect the desired extraction of impurities from the aqueous 1,4-butanediol-containing mixture.

The ratio of hydrocarbon extracting agent to aqueous 1,4-butanediol-containing mixture will vary depending upon the amount of impurities contained in the aqueous butanediol mixture and the degree of removal desired. Generally, a ratio of aqueous 1,4-butanediol to hydrocarbon extracting agent of from about 5:1 to about 1:5 is generally satisfactory, with a ratio of about 2:1 to about 1:2 being preferred. In one embodiment of the process of this invention, the extraction is carried out in a single extraction phase; however, alternate embodiments of the process of this invention involve the deployment of a plurality of extraction zones numbering from 2 to about 5. In such extractions involving multiple extractions zones, it is generally preferable to have countercurrent flow of the hydrocarbon extracting agent. Fresh hydrocarbon extracting agent is contacted with the aqueous 1,4-butanediol-containing mixture in the last extraction stage and the recovered hydrocarbon extract phase is then flowed to the preceeding extraction stage, and so forth. It is equivalently useful to employ parallel flow of the hydrocarbon extracting agent, in which the flow of the hydrocarbon extracting agent is divided such that fresh hydrocarbon extracting agent is contacted with the aqueous butanediol mixture in each of the extraction stages.

The temperature at which the extraction of impurities from the aqueous 1,4-butanediol-containing mixture is effected is not critical. The optimum temperature will depend upon the choice of extracting agent and the nature and quantity of the impurities being extracted. Generally, a temperature in the extraction zone of from 25° C. to about 100° C. is generally satisfactory, with a temperature of about 25° C. to about 50° C. being preferred. The pressure at which the extraction zone is operated is generally any pressure at which the two liquid streams are maintained in the liquid state. Pressures of from about atmospheric pressure to 50 psig are adequate fo this purpose although higher pressures may be employed if desired.

The hydrocarbon extract phase which is recovered from the extraction zone will generally contain γ-hydroxybutyraldehyde, γ-butyrolactone, butyl succinate, butyl butoxy succinate, and a non-volatile residue also referred to as heavies. A small proportion of n-butanol may also be present if the initial distillation of the crude hydrogenation zone product is not efficient. This hydrocarbon extract phase is generally subjected to a distillation to recover the hydrocarbon extracting agent for reuse in the process of this invention. A solvent-free extract is obtained from the bottom of the distillation zone and may be recycled to the hydrogenation zone of a process for converting maleic acid esters to 1,4-butanediol. Inasmuch as this bottoms product from the solvent recovery zone will contain a considerable proportion of non-volatile residue or heavies, it is preferable to take a slip stream representing a portion of this stream and subjecting it to further recovery steps to remove the heavy material. Alternately, a bottoms product may be recovered from the solvent recovery zone which comprises substantially the non-volatile residue or heavies and the bulk of the other aforementioned impurities may be recovered as a side draw product from a portion of the solvent recovery zone above the bottom.

The raffinate phase recovered from the extraction zone comprises 1,4-butanediol, water and a small proportion of some of the more difficult to remove impurities such as γ-butyrolactone and butoxy-1,4-butanediol. This raffinate is introduced to a low pressure distillation zone in which the water is recovered as an overhead product. Any non-volatile residue remaining in the raffinate phase is recovered as a bottoms product from the low pressure distillation zone. 1,4-butanediol is recovered as a side draw product in high purity and substantially free of water. The pressure at which the low pressure distillation zone is operated should be such that the temperature in the bottom of the distillation zone does not exceed about 150° C. At higher temperatures there is an increased degradation of the 1,4-butanediol product which increases the difficulty of obtaining 1,4-butanediol in high purity. The low pressure distillation zone should be operated substantially to exclude the presence of air. Oxygen is known to cause degradation of 1,4-butanediol at elevated temperatures. Therefore, care should be taken in order to ensure that the leakage of air into the low pressure distillation zone is minimized. In an embodiment of the process of this invention, in which the low pressure distillation is carried out in a batch process, it is preferable to blanket the distillation zone with an inert gas, such as nitrogen.

Now reference will be made to the attached Figure which represents a schematic flow diagram of a preferred embodiment of the present invention wherein an aqueous maleic acid-containing mixture is converted to 1,4-butanediol which is recovered in high purity. In this multistep process herein described, n-butanol is illustrated as exemplary of the monohydric alcohol employed. It is to be understood that the Figure is only a schematic representation of the process and does not purport to show the conventional instrumentation present in a typical process.

A maleic acid-containing feedstock is introduced to the esterification-dehydration zone 10 via line 11 wherein it is subjected to a distillation in the additional presence of the monohydric alcohol, e.g. n-butanol, which is introduced into esterification-dehydration zone 10 via line 13. The overhead pressure in the zone is maintained at approximately 80 psig which results in a temperature in the lower portion of the zone of from about 175° C. to about 235° C. There is recovered as an overhead vapor product from the zone a n-butanol-water azeotrope containing approximately 62 wt.% n-butanol. This n-butanol-water azeotrope is condensed in condenser 16 at a temperature of approximately 30° C. and the condensed liquid is allowed to collect in receiver 17 wherein it separates into two immiscible liquid layers. The lower layer is a water-rich layer containing approximately 91 wt. % water and 9 wt.% n-butanol. The upper layer is an alcohol-rich layer containing approximately 79 wt. % n-butanol and 21 wt.% water. The alcohol-rich layer is carried by line 21 to an alcohol recovery zone 20 wherein it is distilled to form an overhead vapor product and a liquid bottoms product comprising substantially n-butanol. The bottoms product is carried by line 25 and combined with the fresh n-butanol in line 13 for reuse in esterification-dehydration zone 10. The overhead vapor product from alcohol recovery zone 20 carried in line 23 (a n-butanol-water azeotrope with a composition similar to that obtained as the overhead product from the distillation zone 10 and carried in line 15) is combined with the n-butanol-water azeotrope in line 15 for condensing in condenser 16.

The water-rich layer recovered from separator 17 is carried via line 27 to dehydrating zone 30 wherein it is subjected to a distillation resulting in an overhead vapor product and a liquid bottoms product comprising substantially water. The overhead vapor product from dehydration zone 30 is a n-butanol water azeotrope with a composition similar to that obtained from esterification-dehydration zone 10 and is carried by line 31 and is combined with the vapor azeotropes carried by line 15 and 23 for condensing in condenser 16. The water obtained as a bottoms product from dehydration zone 30 is carried by line 33 for disposal. The bottoms product from esterification-dehydration zone 10 comprising the crude dialkyl esters of maleic acid, e.g. dibutyl maleate and dibutyl fumarate in admixture with n-butanol and a small amount of other impurities, is recovered via line 19.

The crude dialkyl ester-containing product is carried via line 19 to a first hydrogenation zone 40 wherein it is contacted at elevated temperature and pressure with hydrogen in the presence of a copper chromite hydrogenation catalyst. The reactants and catalyst are maintained under vigorous agitation within the first hydrogenation zone 40 at a temperature of approximately 150° C. and at a hydrogen pressure of approximately 3,000 psig for a period of approximately 20 minutes. The hydrogen pressure is maintained by the addition of high pressure hydrogen via line 42. The reaction product from the first hydrogenation zone 40 now substantially free of ethylenic unsaturation is removed from the zone via line 44.

Additional copper chromite hydrogenation catalyst is added via line 45 to the first hydrogenation zone product in line 44 and the mixture is introduced into a second hydrogenation zone 46 wherein the mixture is contacted with excess hydrogen at elevated temperature and pressure to effect the conversion of the dialkyl esters to 1,4-butanediol. The concentration of copper chromite hydrogenation catalyst in the second hydrogenation zone 46 is approximately 5.0 wt.%, based upon the ester content of the charge to the second hydrogenation zone 46. The temperature is maintained at approximately 250° C. and a hydrogen pressure of approximately 3,600 psig is maintained by the addition of high pressure hydrogen introduced via line 48. The reactants and catalyst are maintained under vigorous agitation within the second hydrogenation zone 46 for a period of approximately 1.5 hours after which the crude reaction mixture comprising 1,4-butanediol is removed from the reaction zone via 49 to a heat exchanger 50 wherein it is cooled to a temperature of approximately 30° C. and is allowed to accumulate in a receiver 52 maintained at a pressure of approximately 3,200 psig. The excess hydrogen gas is vented from receiver 52 via line 54 and is recycled for use in the first hydrogenation zone 40. The liquid product obtained from receiver 52 is carried via line 55 to a catalyst recovery zone 56 wherein the finely divided copper chromite hydrogenation catalyst is recovered by centrifugation and is recovered from the catalyst recovery zone 56 via line 58. The crude 1,4-butanediol-containing product is recovered from the catalyst recovery zone 56 via line 59 and is carried to light ends recovery zone 60 wherein an overhead vapor product comprising n-butanol is obtained in line 61. This overhead butanol-containing product is condensed in heat exchanger 63 and the liquid n-butanol-containing product is collected in receiver 64. A portion of this recovered n-butanol is carried via line 65 to the light ends distillation zone 60 as reflux and the remainder of the recovered n-butanol is carried via line 67 and combined with the recovered n-butanol in line 25 for recycling to the esterification-dehydration zone 10. The bottoms product from the light ends recovery zone 60 comprising crude 1,4-butanediol mixture additionally containing impurities carried by line 68 is diluted with water carried by line 69 to provide an aqueous butanediol-containing mixture having a water content of from about 20 to about 50 wt.%. The aqueous mixture is introduced into the upper portion of extraction zone 70 wherein it is contacted with a hydrocarbon extracting agent in order to remove the impurities from the aqueous butanediol-containing mixture. The hydrocarbon extracting agent is introduced into a lower portion of the extraction zone 70 by line 75. An extract phase containing the impurities extracted from the aqueous butanediol-containing mixture is recovered from the extraction zone 70 in line 77 and a raffinate phase containing the aqueous 1,4-butanediol-containing mixture of reduced impurity level is recovered from the extraction zone 70 in line 79.

The hydrocarbon extract phase is carried by line 77 to an intermediate portion of a distillation zone 80 wherein the hydrocarbon extracting agent is recovered as an overhead product in line 81. A substantially solvent-free extract is recovered from a bottom portion of distillation zone 80 in line 83. The solvent-free extract comprises the impurities extracted from the crude 1,4-butanediol-containing mixture. Typically, the solvent-free extract stream is recycled to the hydrogenation zone of the process wherein the crude 1,4-butanediol is obtained. Inasmuch as the impurities extracted from the crude butanediol product will include a non-volatile residue which is also recovered in distillation zone 80, one embodiment of the process of this invention provides for recovery of the substantially solvent-free extract as a side draw from the distillation zone 80 in line 85 as is illustrated in phantom. In such an embodiment, the non-volatile residue or heavies is recovered from the bottom of distillation zone 80 in line 83.

The raffinate from the bottom of extraction zone 70 is carried via line 79 to an intermediate portion of a low pressure distillation zone 90. In the low pressure distillation zone 90 substantially all of the water contained in the raffinate is recovered as an overhead product in line 91 which is combined with line 69 to provide the water necessary to dilute the crude 1,4-butanediol-containing product as hereinbefore described. A non-volatile residue containing stream is recovered as a bottoms product from the low pressure distillation zone 90 in line 93. 1,4-butanediol is recovered from a side draw of the low pressure distillation zone 90 via line 95.

The overhead operating pressure of the low pressure distillation zone 90 is approximately 15 to 20 mm Hg absolute which results in a comparatively low bottoms temperature of about 150° C. In this manner, thermal degradation of the 1,4-butanediol is minimized. The thermal energy required for the low pressure distillation is provided by conventional means, e.g. a reboiler not shown in the attached figure. The raffinate stream carried via line 79, which is the feed to low pressure distillation zone 90, is passed through heat exchanger 87 wherein it exchanges heat with the overhead product from distillation zone 80 carried via line 81. In this manner, the overall thermal efficiency of the process is maximized.

The above invention is characterized in that the process results in the conversion of the maleic acid and fumaric acid contained in dilute aqueous solutions to 1,4-butanediol which is recovered in high purity. By this invention, 1,4-butanediol is obtained in polymer-grade high purity as is required for its use in the production of polybutylene terephthalate and tetrahydrofuran.

The invention will now be illustrated by the following examples which are for the purposes of illustration and should not be considered a limitation on the scope of the invention.

EXAMPLE 1

A. In a 4 inch dehydrating column equipped with a condenser was added 3,798 g. of n-butanol and the column was brought to reflux. Thereafter, 4,133 g. of an aqueous maleic acid srubber solution consisting of 41.53% maleic acid, 1.01% of a mixture of $C_1$–$C_3$ monocarboxylic acids, 1.01% of carbon compounds (principally formaldehyde) and the balance water, was pumped into the column at a rate of 26 ml/min. After 4.25 hours, 3,004 g. of a water-rich phase and 489 g. of a butanol-rich phase had been collected overhead. 4,263 g. of product in the stillpot had an acid number of 95 mg KOH/g.

B. 1,820 g. of this product and 1,403 g. of n-butanol were placed in a pressure distillation apparatus consisting of a 9.5 ft. × 1 inch steel column packed with Pro-Pak packing and equipped with a 6 liter electrically heated stillpot, a condenser, an accumulator, a reflux pump and back pressure regulator. The column was heated to reflux temperature at a pressure of 56 psig. The distillation was continued for 9 hours during which time 309 g. of dry n-butanol was added to the column and the back pressure was gradually reduced to maintain the stillpot temperature in the range of from 186° C. to 190° C. At the conclusion of the distillation, 811 g. of distillate had been collected and 2,414 g. of bottoms product having an acid number of 0.06 mg KOH/g. was obtained. The product comprised dibutyl maleate and dibutyl fumarate.

EXAMPLE 2

1,816 g. of the product of Example 1A and 1,412 g. of n-butanol were added to the pressure distillation apparatus of Example 1B and distilled at a stillpot temperature of 185°–205° C. for 7.5 hours. 806 g. of overhead distillate were collected and 2,340 g. of product comprising dibutyl esters of maleic acid was obtained. The acid number of the product was 0.09 mg KOH/g.

EXAMPLE 3

The procedure of Example 2, except that the n-butanomaleic acid mixture was brought to reflux in the pressure distillation column with the back pressure regulated to maintain a stillpot temperature of 213°–218° C. After refluxing at this temperature for a period of 4.5 hours, the acid number of the crude ester in the stillpot was found to be 0.19 mg KOH/g.

EXAMPLE 4

In the pressure distillation apparatus of Example 1B were added 5,685 g of n-butanol and the dehydrated maleic acid-containing product obtained by dehydrating 8,967 g of the crude maleic acid scrubber solution containing 34.8% maleic acid in the dehydrating apparatus of Example 1A employing xylene as the dehydrating agent. The distillation column was heated to refluxing temperature at atmospheric pressure and maintained at reflux for 15.5 hours at a pot temperature of 165° C. Water and n-butanol were recovered as an overhead vapor product and condensed and collected in an accumulator. The alcohol-rich upper phase of the material collected in the accumulator was returned to the top of the distillation column as reflux. The acid number of the crude ester contained in the stillpot was measured and found to be 7.1 mg KOH/g and was not further reduced by additional refluxing for 4.5 hours.

EXAMPLE 5

The crude ester product of Example 4 having an acid number of 7.1 mg KOH/g was mixed with sufficient n-butanol to give a 50% solution and was charged to the pressure distillation column. The overhead pressure of the distillation column was maintained at 40 psig and the column was heated to reflux temperature which resulted in a stillpot temperature of 181° C. The overhead vapor product from the distillation column was condensed and the alcohol-rich layer was refluxed as in Example 4. After approximately 5 hours at reflux temperature, a sample was removed from the stillpot and the acid number was found to be 5.0 mg KOH/g The pressure of the distillation column was then increased to 55 psig resulting in a stillpot temperature at reflux of 185°–190° C. After maintaining the column at reflux under these conditions for 3 hours, the acid number of the crude ester product contained in the stillpot was found to be less than 0.25 mg KOH/g

EXAMPLE 6

To illustrate that the esterification of the crude maleic acid mixture is not merely a function of time and temperature, an experiment was conducted wherein the n-butanol-aqueous maleic acid solution was placed in a closed pressure autoclave with a large excess of n-butanol and brought to a temperature of 220° C. Water was not removed from the autoclave during the experiment. After 2 hours at this temperature, a sample was obtained from the autoclave and the acid number of the crude ester-containing product was found to be 4.8 mg KOH/g. It was found that the acid number was not further reduced upon continued heating in this manner. This experiment illustrates that it is imperative that the water concentration of the maleic acid-monohydric alcohol mixture be reduced to very low levels in order for the esterification reaction to proceed to a high degree of completion and to produce an ester product having a low acid number.

EXAMPLE 7

Into a 1 liter magnedrive stirred autoclave was placed 200 g. of dibutyl maleate (reagent grade, Matheson Coleman and Bell) and 30 g. of copper chromite hydrogenation catalyst (Calsicat PC 108-80, Mallinckrodt Chemical Works). The autoclave was charged and pressured to 2,900 psig with hydrogen. Heat was then applied and the temperature was slowly brought to approximately 100° C. at which point an exothermic reaction ensued at a temperature increase to 250° C. Cooling water was passed through the internal coils of the autoclave to control the temperature and not to permit it to exceed about 250° C. After about 5 to 10 minutes the internal temperature had returned to approximately 120° C. and the contents of the autoclave were again heated to a temperature of 200° C. and maintained at this temperature and a hydrogen partial pressure of 2,900 psig for a period of 2.5 hours at which time the reaction appeared to be complete. The contents of the autoclave were then cooled and the hydrogen partial pressure was vented to the atmosphere. The catalyst was separated from the liquid autoclave contents by filtration and the filter was washed with n-butanol. Distillation of the filtrate yielded 1,4-butanediol containing a trace of γ-butyrolactone. Analysis of the filtrate by gas-liquid partition chromatographic techniques indicated that 99% of the dibutyl maleate had been converted to products and that the selectivity to 1,4-butanediol was 90%.

The filtered catalyst was recovered and recycled for reuse. The recovered catalyst weighed approximately 38 g., containing 8 g. of an unknown hydrocarbon material absorbed to the catalyst. 2 g. of fresh copper chromite catalyst were combined with this 38 g. of recovered copper chromite catalyst and employed in hydrogenating approximately 200 g. of dibutyl maleate according to the procedure in part A of this example. The conversion of dibutyl maleate employing this recycled catalyst composition was 99 wt. % with a selectivity to 1,4-butanediol of 94%.

Again, the catalyst was recovered from the reaction product of the second hydrogenation reaction and again recycled for reuse in hydrogenating another approximately 200 g. portion of dibutyl maleate. In this third hydrogenation reaction, the conversion of dibutyl maleate was again 99% and the selectivity to 1,4-butanediol was 97%.

EXAMPLE 8

According to the general procedure of Example 7, a series of runs was made wherein reagent grade dibutyl maleate was hydrogenated at various concentration levels of the copper chromite hydrogenation catalyst employed in Example 7. Catalyst concentrations ranging from 0.5 wt. % to 13.3 wt. % were employed and the results of these runs are listed in the following Table 1.

Table 1

| Wt.% Catalyst | Reaction Time (hours) | Conversion wt.% | Selectivity to 1,4-butanediol |
|---|---|---|---|
| 13.3 | 2.5 | 99 | 97 |
| 6.85 | 2.0 | 97 | 93 |
| 2.43 | 2.0 | 97 | 99 |
| 1.5 | 2.0 | 60 | 88 |
| 0.5 | 2.0 | 46 | 88 |

The reaction conditions employed in each of the runs were a reaction temperature of 200° C., a hydrogen partial pressure of 3,000 psig and a stirring rate of 1400 rpm. From the following data it is apparent that with catalyst concentrations of 2.43 wt. % and higher the conversion levels of dibutyl maleate are near quantitative. At catalyst concentrations of 1.5 wt. % and less the conversion level and selectivity to 1,4-butanediol falls off rapidly.

EXAMPLE 9

A series of runs was made in which a crude dibutyl maleate-containing mixture prepared according to the procedure of Example 2 was hydrogenated according to the procedure of Example 7 in the presence of varying concentrations of copper chromite hydrogenation catalyst. Each of the runs were made at 250° C. and at a hydrogen partial pressure of 3,000 psig and a stirring rate of 500–600 rpm. The composition of the crude pressure esterified starting material employed in Run No. 1 was: dibutyl maleate and dibutyl fumarate 62%, dibutyl butoxysuccinate 38%. In Runs No. 2 to 4 the composition of the starting material was: dibutyl maleate and dibutyl fumarate 78.8%, dibutyl butoxysuccinate 21.2%. The data from the runs are listed in the following Table 2. The conversion figures represent the percent of all the esters present. From the data it is apparent that at a reaction time of 1 hour, a catalyst concentration of from about 10 to about 15 wt. % is required to attain near quantitative conversions of the esters to 1,4-butanediol.

Table 2

| Run No. | Wt.% Catalyst | Reaction Time (hours) | Conversion wt.% | Selectivity to 1,4-butanediol |
|---|---|---|---|---|
| 1 | 5 | 1.0 | 86 | 88 |
| 2 | 10 | 1.0 | 94 | 87 |
| 3 | 15 | 1.0 | 99 | 90 |
| 4 | 15 | 0.67 | 94 | 95 |

EXAMPLE 10

A series of runs was carried out wherein the stirring rate expressed as rpms, of the magnedrive stirred autoclave was investigated for hydrogenations of dibutyl maleate according to the general procedure of Example 7. In each of the following runs the hydrogenation reaction was carried out at 200° C. and at a hydrogen partial pressure of 3,000 psig in the presence of 2.43% by weight of the copper chromite hydrogenation catalyst employed in Example 7. The data are presented in the following Table 3. From the data contained in the Table, it is apparent that as the stirring rate is reduced, the conversion level and selectivity to 1,4-butanediol decrease and that at very low stirring rates even an increase in reaction temperature and catalyst composition will not maintain the high conversion levels desired.

Table 3

| Stirring Rate (rpm) | Reaction Time (hours) | Conversion wt.% | Selectivity to 1,4-butanediol |
|---|---|---|---|
| 1400 | 2.0 | 97 | 99 |
| 1000 | 3.75 | 87 | 97 |
| 500 | 2.0[1] | 94 | 76 |
| 250 | 2.0[2] | 46 | 88 |

[1]Reaction temperature 225° C.
[2]Reaction Temperature 225° C.; 5% by weight catalyst

EXAMPLE 11

A series of runs was made wherein the effect of hydrogen partial pressure on the hydrogenation of the dialkyl esters of maleic and fumaric acid to 1,4-butanediol was evaluated. In these series of runs both pure dibutyl maleate and a crude pressure esterified dialkyl ester-containing product prepared according to the procedure of Example 1 were each evaluated as the feedstock material. The data for these runs are presented in the following Table 4.

Table 4

| Reactant | Hydrogen Partial Pressure psig | Conversion wt.% | Selectivity to 1,4-butanediol |
|---|---|---|---|
| 1) | 2000 | 99 | 77 |
| 1) | 3000 | 99 | 98 |
| 2) | 3000 | 99 | 92 |
| 2) | 3500 | 97.5 | 99 |
| 2) | 4000 | 96 | 93 |

1) Pure dibutyl maleate; reaction conditions 200° C. for 2.0 hours using 13% by weight copper chromite catalyst.
2) Crude pressure esterified product of Example 1: reaction conditions 250° C. for 1.0 hour using 5% by weight copper chromite catalyst.

For the pure dibutyl maleate a hydrogen partial pressure of 3,000 psig results in a near quantitative conversion of the ester to 1,4-butanediol while at lower hydrogen partial pressures the conversion is still high but the selectivity to 1,4-butanediol decreases. For the crude pressure esterified ester-containing feedstock a slightly higher hydrogen partial pressure appears to be required in order to attain the same selectivity for production of 1,4-butanediol as experienced with the pure dibutyl maleate feedstock.

EXAMPLE 12

A series of runs was carried out wherein the crude pressure esterified dialkyl ester-containing product prepared according to Example 1 was hydrogenated in the presence of 5 wt. % copper chromite hydrogenation catalyst and at a hydrogen partial pressure of 3,000 psig at various reaction temperatures. The data from these series of runs are presented in the following Table 5.

Table 5

| Temperature, ° C. | Time (hours) | Conversion wt.% | Selectivity to 1,4-butanediol |
|---|---|---|---|
| 220 | 1.6 | 99 | 84 |
| 250 | 1.5 | 98 | 83 |
| 275 | 1.0 | 98 | 93 |

The data demonstrate that at temperatures in the range of 220° C. to 275° C. the conversion level of the ester-containing feedstock is near quantitative and that the selectivity to 1,4-butanediol seems to decrease with increasing contact time in the hydrogenation reaction zone.

EXAMPLE 13

A series of runs was carried out according to the general procedure of Example 7 wherein various dibutyl maleate-containing feedstocks of varying acid numbers were employed in the process. In each run the hydrogenation reaction was carried out at a temperature of 225° C. at a hydrogen partial pressure of 3,000 psig for the time indicated. The copper chromite hydrogenation catalyst employed in Example 7 was used in an amount of 5% by weight based on the ester feedstock. The data from these runs are presented in the following Table 6.

Table 6

| Acid Number Of Feedstock mg KOH/g | Reaction Time hours | Conversion wt.% | Selectivity to 1,4-butanediol |
|---|---|---|---|
| 5.5 | 2.0 | 10 | 15 |
| 1.0 | 1.3 | 94 | 89 |
| 0.4 | 1.5 | 99 | 95 |
| 4.7[1] | — | 43 | — |

[1]This dibutyl maleate feedstock was prepared by reacting n-butanol with maleic acid employing p-toluene sulfonic acid as a catalyst. The ester contained 912 ppm sulfur impurities. The reaction conditions employed in this run were 200° C. and 6.8 wt.% catalyst.

From an examination of the data it is apparent that ester-containing feedstocks having an acid number greater than about 1.0 mg KOH/g are not effective in hydrogenating such ester-containing feedstocks to 1,4-butanediol. In the last run listed in Table 6, it is to be noted that not only was the conversion level low due to the high acid number of the ester feedstock but also the catalyst was inactivated during the run as a result of the sulfur present in the ester feedstock.

EXAMPLE 14

A series of runs was made according to the general procedure of Example 7, employing as a starting material 200 g. of a crude dibutyl butoxy succinate-containing material having the following composition: 45% dibutyl butoxy succinate and 55% of a mixture of dibutyl maleate and dibutyl fumarate. In each run, 5% by weight of a copper chromite hydrogenation catalyst (No. PC 108-80, Calsicat Division of Mallinckrodt Chemical Works) was added to the autoclave and the autoclave was pressurized with hydrogen and heated to 250° C. In each run, the autoclave contents were intimately admixed by stirring for 1 hour at a particular hydrogen pressure after which the contents of the autoclave were recovered and analyzed for conversion of materials to 1,4-butanediol. In the following Table 7, the conversion figure refers to the conversion of all the esters present (dibutyl butoxy succinate, dibutyl maleate and dibutyl fumarate). The selectivity is that for 1,4-butanediol as obtained from both materials.

Table 7

| Run No. | Pressure | Temperature | Conversion % | Selectivity |
|---|---|---|---|---|
| 1 | 2000 | 250 | 99 | 92 |
| 2 | 3000 | 250 | 99 | 92 |
| 3 | 3500 | 250 | 97.5 | 99 |
| 4 | 4000 | 250 | 96 | 93 |
| 5 | 3000[1] | 220 | 99 | 84 |
| 6 | 3000[2] | 250 | 98 | 83 |
| 7 | 3000 | 275 | 98 | 93 |

[1]Reaction time 1.6 hours
[2]Reaction time 1.5 hours

EXAMPLE 15

According to the general procedure of Example 14, 225.5 g. of a mixture containing 2-butoxy-1,4-butanediol (an intermediate representing the partial hydrogenation of dibutyl butoxy succinate) and dibutyl butoxy succinate were placed in a stirred pressure autoclave with 1.20 g. of copper chromite catalyst and heated for 1.5 hours. Thereafter, the autoclave contents were recovered and analyzed and the data are presented in the following Table 8.

Table 8

| Compound | Composition, wt.% Feedstream | Product |
|---|---|---|
| n-butanol | 69.5 | 69.9 |
| 1,4-butanediol | 20.0 | 28.2 |
| γ-butyrolactone | — | 1.0 |
| dibutyl succinate | 1.1 | 1.0 |
| 2-butoxy-1,4-butanediol | 5.7 | trace |
| dibutyl butoxy succinate | 3.7 | trace |

The data indicate that the process of this invention is effective for conversion of 2-butoxy-1,4-butanediol and dibutyl butoxy succinate to 1,4-butanediol in substantially quantitative conversions even when these materials are present only in relatively small amounts with other noninterfering materials.

EXAMPLE 16

According to the general procedure of Example 14, 279.5 g. of a 2-butoxy-1,4-butanediol-containing mixture was placed in a stirred autoclave along with 15.0 g. of copper chromite catalyst. The autoclave was then heated to 250° C. under 3,000 psig of hydrogen pressure and maintained under these conditions for 1 hour. Thereafter, the autoclave contents were recovered and analyzed for conversion of the 2-butoxy-1,4-butanediol to 1,4-butanediol and n-butanol. The composition of the starting material and the reduced product are presented in the following Table 9.

Table 9

| Compound | Composition, wt.% Feedstream | Product |
|---|---|---|
| n-butanol | 5.61 | 42.9 |
| γ-butyrolactone | — | 2.53 |
| 1,4-butanediol | 8.78 | 40.29 |
| 2-butoxy-1,4-butanediol | 78.4 | 1.28 |

Table 9-continued

| Compound | Composition, wt.% Feedstream | Product |
|---|---|---|
| non-volatile material | 8.0[a] | 13.0[a] |

[a]The weight percent of the non-volatile material was obtained by difference of the total from 100% and is approximate.

EXAMPLE 17

In this example, 300 g. of a crude 1,4-butanediol was diluted with 300 g. of water and subjected to three extractions employing 100 ml of hexane in each extraction. The composition of the crude butanediol and the final purified 1,4-butanediol after the three extractions are presented in the following Table 10. The breakdown of the percent removal of contaminants in each of the three extraction stages is presented for two of the key components, dibutyl succinate and butoxy dibutyl succinate.

Table 10

| | Crude 1,4-butanediol | Product 1,4-butanediol* |
|---|---|---|
| n-butyl alcohol | 4.39 | Trace |
| γ-butyrolactone | 0.26 | 0.24 |
| 1,4-butanediol | 87.27 | 95.17 |
| γ-hydroxybutyraldehyde | 0.32 | 0.39 |
| dibutyl succinate | 2.62 | Trace |
| 2-butoxy-1,4-butanediol | 4.08 | 4.20 |
| butoxy dibutyl succinate | 0.86 | Trace |

*water excluded from the analysis

| | % Ester Removed Per Extraction | | |
|---|---|---|---|
| | 1st | 2nd | 3rd |
| dibutyl succinate | 89.0 | 10.0 | 0.9 |
| butoxy dibutyl succinate | 90.0 | 9.7 | Trace |

The aqueous product 1,4-butanediol obtained from the three extractions was subjected to a low pressure distillation to remove the water. 1,4-butanediol with a purity of approximately 99.7% and uncontaminated with ester was obtained as a final product. In this distillation, 259 g. of the crude 1,4-butanediol were distilled in an 1 inch × 33 inch distillation column with an operating pressure of 15 mm Hg. A number of cuts were obtained throughout the distillation and analyzed for 1,4-butanediol and impurities. The data are presented in the following Table 11, which data does not include the proportion of water in the overhead cuts. The data indicate that approximately 66% of the crude 1,4-butanediol is recoverable as a high purity 1,4-butanediol product. By comparison, a low pressure distillation was attempted with a crude 1,4-butanediol mixture which had not been subjected to the extraction process of this invention. The data for this distillation is presented in the following Table 12. From an analysis of the data contained therein, it is apparent that approximately only 10% of the 1,4-butanediol contained in the crude diol mixture was recoverable in a purity exceeding 95%.

In a comparable extraction employing benzene as the hydrocarbon extracting agent, 61% of the 1,4-butanediol was recovered from the raffinate in a purity exceeding 99.5%.

TABLE II

Distillation of Hexane Extracted 1,4-Butanediol
Distribution of Components, Wt.%

| Cut No. | Wt. g. | Total % Ovhd. | Pot Temp. °C. | n-Butyl Alcohol | unknown | γ-Butyro-lactone | 1,4-Butane-diol | (γ-Hydroxy-butyral-dehyde) | Dibutyl Succinate | Dibutyl Fumarate |
|---|---|---|---|---|---|---|---|---|---|---|
| 1 | 15 | 5.8 | 151 | 0.15 | .02 | 1.24 | 95.8 | 2.6 | 0.10 | 0.07 |
| 2 | 17.5 | 12.6 | 151 | 0.03 | | 0.17 | 98.8 | 1.0 | | |
| 3 | 16.0 | 18.8 | 151 | 0.03 | | 0.44 | 99.3 | 0.5 | | |
| 4 | 5.5 | 20.9 | 151 | 0.20 | | 0.64 | 98.6 | 0.7 | | |
| 5 | 14.0 | 26.3 | 153 | 0.10 | | 0.94 | 98.2 | 0.7 | | |
| 6 | 15.0 | 32.1 | 153 | 0.05 | | 0.24 | 99.5 | 0.4 | | |
| 7 | 18.0 | 39.0 | 154 | 0.07 | | 0.19 | 99.7 | 0.03 | | |
| 8 | 15.0 | 44.8 | 155 | 0.05 | | 0.19 | 99.7 | 0.05 | | |
| 9 | 17.0 | 51.4 | 155 | 0.07 | | 0.22 | 99.7 | | | |
| 10 | 13.0 | 56.4 | 155 | 0.05 | .01 | 0.24 | 99.7 | | | |
| 11 | 12.5 | 61.2 | 155 | 0.06 | .02 | 0.18 | 99.8 | | | |
| 12 | 15.5 | 67.2 | 155 | 0.11 | .11 | 0.56 | 99.2 | | | |
| Undist. Fract. | 85.0 | | | | | | | | | |

TABLE 12

| Cut No. | Wt. g. | H₂O | THF | n-Butyl Alcohol | Dibutyl Formal | γ-Butyro-lactone | 1,4-Butane-Diol | γ-Hydroxy Butyral-dehyde | Dibutyl Succ-inate | Dibutyl Mal-eate | Butoxy-1,4-butane-Diol | Butoxy dibutyl Succinate | Unknown |
|---|---|---|---|---|---|---|---|---|---|---|---|---|---|
| 1 | 52.0 | 31.7 | 1.6 | 63.2 | 0.1 | | | | | | | | 3.4 |
| 2 | 125.0 | 0.9 | | 98.9 | 0.09 | | | | | | | | 0.04 |
| 3 | 139.0 | 0.3 | | 99.7 | 0.03 | | | | | | | | |
| 4 | 388.5 | | | 99.9 | | | | | | | | | |
| 5 | 13.0 | | | 49.1 | 17.2 | 6.4 | | | | | | | 27.3 |
| 6 | 18.0 | 0.2 | | 3.2 | | 63.2 | 13.9 | 12.6 | | | | | 7.0 |
| 7[1] | 60.9 | | | 1.1 | | 4.2 | 6.1 | 0.6 | 85.3 | 0.2 | | | 2.6 |
| 8 | 18.7 | | | 3.5 | | 6.4 | 71.5 | 2.5 | 14.8 | 0.3 | 1.0 | | |
| 9 | 26.4 | | | | | 1.6 | 88.1 | 3.4 | 4.1 | 0.2 | 2.6 | | |
| 10 | 25.0 | | | 1.5 | | 1.7 | 84.6 | 0.7 | 1.1 | 0.5 | 9.8 | | |
| 11 | 30.5 | | | 0.2 | | 2.2 | 84.5 | 0.8 | | | 12.1 | | |
| 12 | 36.0 | | | 0.3 | | 0.5 | 91.6 | 0.4 | | | 7.2 | | |
| 13 | 37.0 | | | 0.5 | | 0.7 | 87.4 | 0.2 | | 0.2 | 11.4 | | |
| 14 | 36.5 | | | 0.2 | | 0.5 | 94.0 | 0.1 | | | 5.2 | | |
| 15 | 25.7 | | | 0.3 | | 0.4 | 97.1 | trace | | | 2.2 | | |
| 16 | 22.2 | | | 0.6 | | 0.2 | 98.0 | | | | 1.2 | | |
| 17 | 34.7 | | | 0.2 | | 0.2 | 99.6 | 0.04 | | | | | |
| 18 | 29.6 | | | 0.3 | | 0.3 | 98.7 | trace | | | 0.4 | | 0.3 |
| Btms Col.[2] | 68.0 | | | | | 0.2 | 19.2 | 0.5 | | | 80.2 | | |
| Hold-up | 15.0 | | | | | | 99.0 | | | | | | |
| Total Wt. | | 18.11 | 0.8 | 693.2 | 18.6 | 332.6 | 3.1 | 58.4 | 0.4 | 54.6 | 17.1 | | |
| Mole% Comp. Excl. of n-Butyl Alcohol and Unk. | | | | | 0.2 | 4.97 | 79.89 | 0.86 | 5.40 | 0.4 | 7.34 | 1.30 | |

[1]Top phase removed from continuous decantor
[2]Composition of column holdup assumed to be 99% diol.

EXAMPLE 18

To a mixture of 10 g of water and 16.9 g. of crude 1,4-butanediol (88.8% by weight butanediol, 5.79% butyrolactone and 5.34% butyl succinate) was added 10 g. of benzene. The mixture was mixed and the benzene phase allowed to separate. The benzene phase consisted of 1.93% butyrolactone, 0.38% butanediol, 6.21% butyl succinate and 91.46% benzene. From this data, it can be seen that 19.4% of the butyrolactone and 67.32% of the butyl succinate were extracted from the starting blend. Only 0.24% of the butanediol was extracted with the benzene extracting agent.

EXAMPLE 19

By a procedure similar to that of Example 2, a crude 1,4-butanediol-containing mixture was subjected to five extractions of equal volumes of benzene. The extraction was done on the crude 1,4-butanediol mixture after removing any butyl alcohol. The data in the following Table 13 demonstrate that a very high percentage removal of esters are achieved from the crude diol mixture. It is also apparent that benzene is particularly effective in removing γ-hydroxybutyraldehyde and γ-butyrolactone from the crude diol mixture.

Table 13

| | Crude 1,4-butanediol | Raffinate Phase, g. | Extract Phase, g. |
|---|---|---|---|
| 1,4-butanediol | 600.9 | 594.0 | 6.9 |
| γ-hydroxybutyraldehyde | 4.0 | 0.36 | 3.6 |
| γ-butyrolactone | 23.1 | 4.2 | 18.9 |
| dibutyl fumarate | 45.7 | — | 45.7 |
| dibutyl succinate | 56.6 | 0.03 | 56.6 |
| dibutyl butoxy succinate | 34.6 | 0.05 | 34.6 |
| butoxy-1,4-butanediol | 47.0 | 45.8 | 1.2 |
| non-volatile residue | 70.8 | 22.2 | 48.6 |
| | 882.7 | 666.64 | 216.1 |

The high purity 1,4-butanediol product had the following properties:

| Freeze point | 20.1° C. |
|---|---|
| Initial color, Hazen | 10 |
| Water content | |

|   |   |
|---|---|
| (C. Fisher method) | 0.08 |
| After heating 4 hours at 190–195° C. | |
| Color | 10 |
| Odor | None |
| Water (C. Fisher) | 0.16 |

We claim as our invention:

1. A process for the production of 1,4-butanediol from a maleic acid-containing feedstock, which process comprises the steps of:
   a. contacting the maleic acid-containing feedstock with a monohydric alkanol having from 2 to about 10 carbon atoms in an esterification-dehydration zone comprising a pressure distillation column wherein the maleic acid-containing feedstock is distilled in the presence of the monohydric alkanol thereby forming an overhead vapor product comprising an azeotrope of water and the monohydric alkanol and a bottoms product having an acid number of 1.0 mg KOH/g. or less comprising the monohydric alkanol and the dialkyl ester of maleic acid,
   b. contacting the bottoms product from the esterification-dehydration zone with hydrogen at elevated temperature and pressure in the presence of a copper chromite hydrogenation catalyst in a first hydrogenation zone thereby to hydrogenate the ethylenic unsaturation present in the bottoms product from the distillation zone,
   c. contacting the product from the first hydrogenation zone in a second hydrogenation zone with hydrogen in the presence of a copper chromite hydrogenation catalyst thereby to reduce the dialkyl esters to a product comprising 1,4-butanediol and monohydric alkanol,
   d. introducing the product from the second hydrogenation zone to a catalyst recovery zone wherein the copper chromite hydrogenation catalyst is recovered,
   e. introducing the product obtained from the catalyst recovery zone to a light ends recovery zone wherein there is recovered an overhead product comprising the monohydric alkanol and the more volatile impurities and a bottoms product comprising crude 1,4-butanediol and the less volatile impurities, and recovering 1,4-butanediol from said bottoms product of the light ends recovery zone.

2. The process according to claim 1 wherein the monohydric alkanol is primary isoamyl alcohol or n-amyl alcohol.

3. The process according to claim 1 wherein the monohydric alkanol is n-butanol.

4. The process according to claim 3 wherein the first hydrogenation zone is maintained at a temperature of from about 100° C. to about 300° C. and at a hydrogen partial pressure of from about 2,000 psig to about 3,500 psig and wherein the second hydrogenation zone is maintained at a temperature of from about 200° C. to about 300° C. and at a hydrogen partial pressure of from about 2,500 psig to about 3,500 psig.

5. The process according to claim 1 wherein the copper chromite hydrogenation catalyst recovered from the product of the second hydrogenation zone is recycled for reuse.

* * * * *